United States Patent
Spitznagle

(10) Patent No.: US 6,567,990 B1
(45) Date of Patent: May 27, 2003

(54) ELECTROMYOGRAPHIC EXAMINATION GLOVE

(76) Inventor: Richard James Spitznagle, 622 Waterford View Ct., Manchester, MO (US) 63021

( * ) Notice: Subject to any disclaimer, the term of this patent is extended or adjusted under 35 U.S.C. 154(b) by 0 days.

(21) Appl. No.: 10/082,724

(22) Filed: Feb. 26, 2002

(51) Int. Cl.[7] .............................................. A41D 19/00
(52) U.S. Cl. .......................................... 2/161.7; 2/160
(58) Field of Search ..................... 2/160, 161.6, 161.7, 2/163, 169, 21; 600/372, 373, 591

(56) References Cited

U.S. PATENT DOCUMENTS

| | | | | |
|---|---|---|---|---|
| 4,245,656 A | * | 1/1981 | Farr et al. ....................... | 2/160 |
| 4,542,753 A | * | 9/1985 | Brenman et al. ............... | 29/825 |
| 5,067,478 A | * | 11/1991 | Berlant ......................... | 601/134 |
| 5,070,862 A | * | 12/1991 | Berlant ......................... | 601/21 |
| 5,867,831 A | * | 2/1999 | Husain ......................... | 2/161.7 |
| D459,816 S | * | 7/2002 | Perricone ...................... | D2/621 |

* cited by examiner

Primary Examiner—John J. Calvert
Assistant Examiner—Katherine Moran

(57) ABSTRACT

The invention is an electrode glove used for internal muscle performance evaluation especially for the pelvic floor and rectal muscle groups. The intent is to combine a clinician's sense of touch with his or her knowledge of muscle location to obtain more accurate and rich muscle performance information. Using this device a clinician will know whether contraction readings are from the muscle(s) desired and not surrounding muscles, which side is being read and at what muscle fiber depth. The device is an assembly consisting of (1) an examination glove and (2) surface electrodes attached to the index finger.

1 Claim, 1 Drawing Sheet

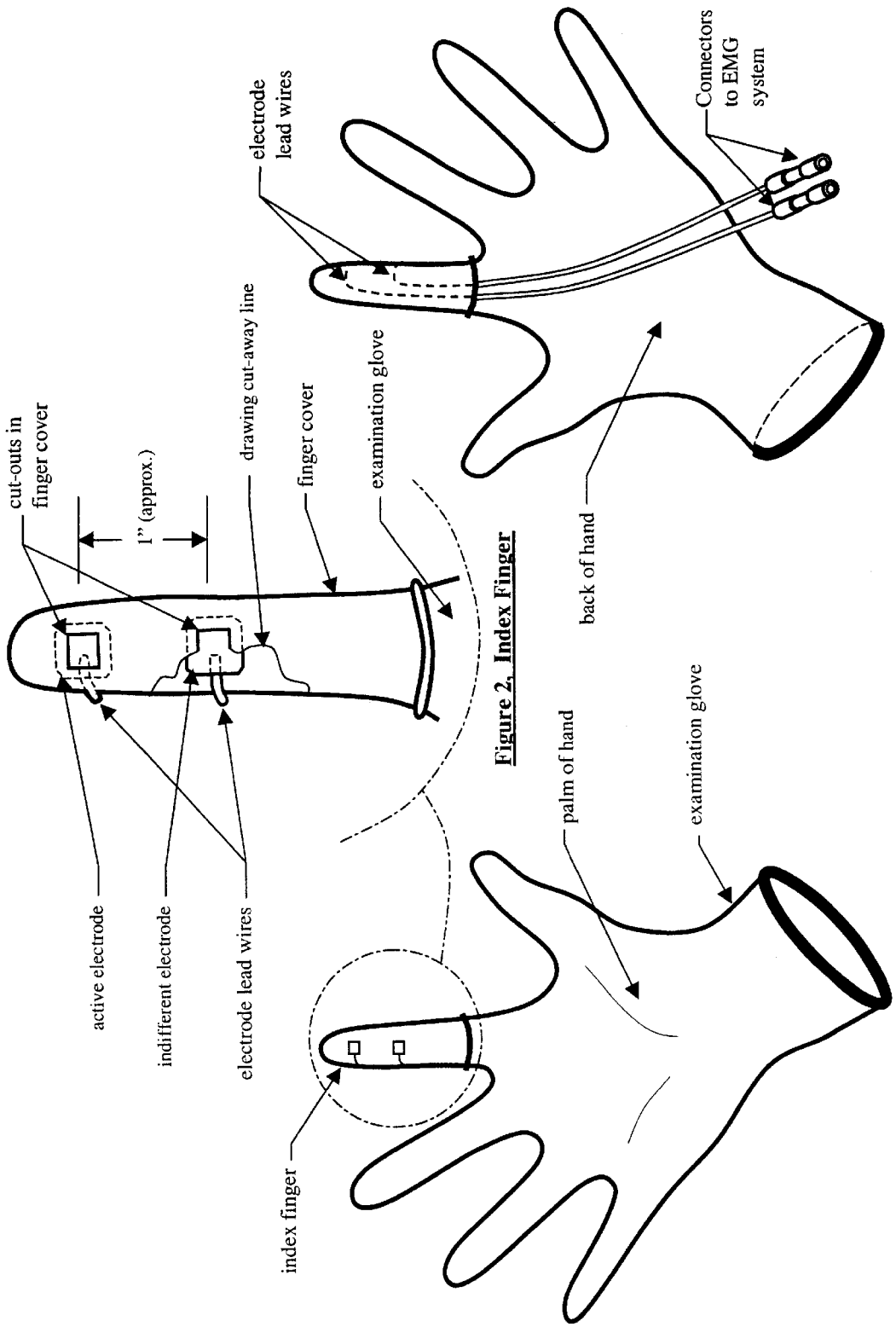

ELECTROMYOGRAPHIC EXAMINATION GLOVE

CROSS-REFERENCE TO RELATED APPLICATIONS

Not Applicable

FEDERALLY SPONSORED RESEARCH OR DEVELOPMENT

Not Applicable

REFERENCE TO SEQUENCE LISTING, TABLE, PROGRAM LISTING CD APPENDIX

Not Applicable

BACKGROUND OF THE INVENTION

The field to which this invention pertains is the pelvic floor and rectal muscle evaluation. Often, in evaluating incontinence, pelvic pain, or sexual dysfunction, an evaluation of a specific muscle of the pelvic floor or rectum is conducted. With female urinary incontinence, pelvic pain, or sexual dysfunction this evaluation is conducted on muscles that are palpated vaginally. With fecal and male urinary incontinence the evaluation is conducted on muscles that are palpated rectally.

When a muscle contracts it produces a small amount of electrical current. To determine the level to which a specific muscle is contracting, this current is read with a pair of electrical muscle activity sensing, electromyographic (EMG) surface electrodes. They serve as conductors and link the body to an EMG system, which displays electrical current intensity. Weak current as read by the electrodes implies poor muscle performance. If poor muscle performance is found it often becomes the focus of rehabilitation.

Today there are two styles of electrical sensing EMG electrodes used in this application, surface electrodes and probe electrodes. Surface electrodes are placed external to the area being evaluated, typically in the lower abdominal region. They are flat and are normally held onto the skin by conductive adhesive. Probe electrodes consist of non-metallic cylindrical bodies with exposed electrodes on the probe surface. They are placed vaginally or rectally. Vaginal probe electrodes are often referred to as "perineometers". Both types have electronic lead wires that connect to an EMG system.

Surface electrodes, not being in contact with the muscle to be evaluated, provide a global reading of the entire pelvic floor or rectal area. With their use it is difficult to determine whether the readings are those of the desired muscle or those of neighboring muscles. The clinician must be very specific in directing the patient to contract a desired muscle and determine whether the reading is the result of it alone. For these reasons, surface electrode readings are subject to assumptions and can therefore be unreliable.

Since probes are used internally, closer to the desired muscle and not aimed at the entire region, they reduce the effects of readings from neighboring muscles. Probes therefore perform better than surface electrodes. Probe electrodes do however have some limitations.

Some limitations with probes arise from the fact that not all patients have the same cavity contour, muscle size and muscle location. Some cavities have more curvature than do others. The fixed shape of existing probes can therefore lead to readings of undesired neighboring muscles. Likewise, since pelvic floor and rectal muscles are not all located at the same depth from the cavity opening and muscle size can vary from patient to patient the clinician must judge the correct depth to insert the device to avoid readings of neighboring muscles.

Other problems with probes are that even when properly positioned for the desired muscle, it is impossible to determine if contractions of other muscles in the immediate region has also occurred affecting the EMG reading. Also, it impossible to determine whether the reading is from superficial or deep muscle activity. Finally, since the probe electrodes are cylindrical, encompassing the entire probe circumference, the clinician is unable to determine whether a muscle reading is coming from the patient's right or left side. Probe electrodes are more reliable than surface electrodes because they are closer to the electrical source, but like surface electrodes produce readings that lack detail. As with surface electrodes, a degree of speculation accompanies their readings.

Because they are somewhat more accurate than surface electrodes, probes electrodes are preferred. Probe electrodes however, are considerably more expensive than surface electrodes (approximately $30 compared to $1). They can be reused for the same patient over the life of treatment, but not being considered disposable due to cost, an initial patient evaluation is usually done with surface electrodes. Only after this initial evaluation warrants is a probe electrode typically prescribed.

What is needed in this field is an internal EMG device with a small electrode that can be reliably placed on a specific muscle, on a particular patient side (left or right). This same device needs to be able to distinguish whether a muscle reading is being influenced by the contractions of other muscles in the region and whether the muscular activity read is superficial or deep, preferably at a disposable cost.

BRIEF SUMMARY OF THE INVENTION

The objective of the invention was to create a pelvic floor/rectal electromyography (EMG) device whose readings were more reliable and interpretable than those of existing surface electrode and probe devices. The problems related to these existing devices are that clinicians cannot determine whether 1.) the electrode is contacting and therefore reading the desired muscle, 2.) the reading is being influenced by neighboring muscles, 3.) the reading is from the left or right side of the muscle and 4.) the reading is from superficial or deep muscles.

Because there is a difference in the anatomy of every patient and that pelvic floor muscles cannot be found by sight, the best way for a clinician to find a specific muscle on a given patient is by touch. Clinicians, typically Physical Therapists and Urogynecologists, are trained in muscular anatomy. They know haw to identify a muscle by its physical characteristics and by its proximity to other muscles and can sense whether muscle contractions are coming from superficial or deep muscle fibers.

Being the best method of muscle identification, it was desirable to incorporate a clinicians sense of touch and his or her knowledge of anatomy into a pelvic floor/rectal EMG device. Incorporating touch, a clinician can produce more reliable and more meaningful electronic signal readings. For these reasons, the Electromyographic Examination Glove was developed.

The device consists of EMG electrodes attached to the index finger of an examination glove. The active electrode is located at the tip of the index finger. This allows the clinician to simultaneously find the desired muscle using touch and place the active electrode directly on it. During the evaluation of the muscle's contractions, the clinician can therefore be certain that the readings being observed are those of the desired muscle. Also, by incorporating an exam glove, the inadvertent contractions of neighboring muscles can be felt and those readings ignored. A single electrode at the tip of the index finger also allows independent readings from both right and left sides of the muscle. Lastly, the clinician can feel whether the readings are coming from superficial or deep muscle fibers, which is knowledge that may alter the course of treatment.

BRIEF DESCRIPTION OF DRAWING VIEWS

FIG. 1, Glove—Palm Side Shows the palm side of the glove and the location of the electrodes FIG. 2, Index Finger Shows a detail view of the index finger, where the electrodes are attached, the approximate spacing of the electrodes and the finger cover option for holding the electrodes in place FIG. 3, Glove—Back Side Shows the back of the glove, electrode lead wires and EMG system connectors

DETAILED DESCRIPTION OF THE INVENTION

The invention consists of an examination glove combined with two electrical muscle activity sensing, electromyographic (EMG) surface electrodes. These EMG electrodes are designed to read ionic activity of various muscle states.The electrodes serve to link a muscular electronic signal to a reading system, which is not part of the invention. The active electrode is placed at the tip of the index finger where the clinician will be examining the muscle to be read. The indifferent electrode is placed approximately one inch away. Since the indifferent electrode must also contact the patient, it cannot be placed too far away from the active electrode. However, if the indifferent electrode is placed too close to the active electrode it will short out the signal. To keep the electrodes in place on the glove, a finger cover is used. It contains cut outs to allow exposure of the sensing surface of the electrodes. The lead wires of the electrodes run along the back of the glove so as not to interfere with the clinician's ability to perform the exam. Design options to the finger cover include applying mesh tape over the electrode, an outer glove with electrode cut outs, bonding the electrodes to the glove or forming the electrodes into the glove.

The examination glove can be of any typical glove material such as latex or vinyl. Latex examination gloves are typically thinner which offer greater touch sensitivity. Thicker vinyl gloves can be used where greater protection of the clinician is desired or where an allergy to latex exists. The gloves can be made with powdered interiors for ease of installation and removal. They can also be made in several sizes and in left and right hand models.

The surface electrodes can be any variety suitable for internal usage. It is desired that they be as thin as possible to increase the sensitivity of touch during their usage. Since larger electrodes pick up more surrounding electrical activity and it is desired to keep spacing between the two at approximately 1 inch, the size of the electrode should be small, approximately ½ inch by ½ inch. The muscle contact area of the electrodes could be further reduced by finger-cover cut outs that are less than the ½ inch by ½ inch electrode size. Direct lead style electrodes are desired. Snap or "alligator clip" lead connections are too bulky to effectively fit the glove assembly.

To use the glove the clinician simply selects a model designed for his or her dominant hand. The glove is placed over the hand so that the electrodes are on the finger tip side of the index finger. The electrode leads are connected to an EMG system. The pelvic floor or rectal muscle to be examined is found by touch with the tip of the index finger. In doing so the active Hi electrode is in proper muscular contact. The indifferent electrode is verified to be in contact with the patient. The patient is asked to contract the desired muscle. If the proper muscle is contracted, the clinician notes the EMG reading along with which muscle side, left or right, and muscle depth the contraction relates. If the clinician detects by touch that an undesired muscle has contracted or that other muscles in addition to that desired have contracted, the EMG reading is ignored. From an accurate EMG reading of the desired muscle a treatment plan is prescribed.

The novelty of the Electromyographic Examination Glove invention is that it combines a clinician's sense of touch during a pelvic floor or rectal muscle exam with an ability to quantitatively read the electronic muscle activity level through an external EMG device. With it, a clinician can not only gather muscle activity level readings but through his or her sense of touch at the location of the device's active electrode determine 1. to which muscle the readings correspond, 2. whether unintended muscles have contracted contaminating the readings and 3. whether the readings were from superficial or deep muscle fibers. These three clinically relevant aspects are indiscernible with existing surface and probe style electrodes because they do not incorporate the clinician's sense of touch.

I claim:

1. A wearable, fingertip, pelvic floor and rectal electromyographic (EMG) examination device for sensing electrical muscle activity levels, that allows for quantitative measurements when connected to an EMG system, which through incorporating the clinicians sense of touch at the active electrode allows device placement on the specific muscle to be read, knowledge of the muscle fiber depth of the activity and whether inadvertent contracting of neighboring muscles has occurred thereby degrading the reading, which is comprised of:

a.) An active electrical muscle activity sensing, EMG surface electrode designed to read low ionic activity in the electrical range of various muscle states at a fingertip location with connection means to an EMG system, b.) An indifferent EMG surface electrode designed to read low ionic activity in the electrical range of various muscle states located in close proximity to the active electrode with connection means to an EMG system, c.) An insulated, flexible glove onto which the sensing EMG electrodes are either formed, bonded or held in place with an added finger cover that contains cut outs for electrode surface exposure.

* * * * *